United States Patent [19]
Bajzar et al.

[11] Patent Number: 5,993,815
[45] Date of Patent: Nov. 30, 1999

[54] METHODS AND COMPOSITIONS FOR INHIBITING THE ACTIVATION OF THROMBIN-ACTIVATABLE FIBRINOLYSIS INHIBITOR (TAFI)

[75] Inventors: Laszlo S. Bajzar; Michael E. Nesheim, both of Kingston, Canada; William R. Church, Winooski, Vt.

[73] Assignee: University of Vermont, Burlington, Vt.

[21] Appl. No.: 08/966,432

[22] Filed: Nov. 7, 1997

Related U.S. Application Data

[60] Provisional application No. 60/030,721, Nov. 8, 1996.

[51] Int. Cl.$^6$ .................................................. A61K 39/395
[52] U.S. Cl. ..................................... 424/145.1; 424/133.1; 424/135.1; 424/146.1; 530/387.3; 530/388.25; 530/388.26
[58] Field of Search .............................. 424/145.1, 133.1, 424/135.1, 146.1; 530/388.25, 387.3, 388.26

[56] References Cited

U.S. PATENT DOCUMENTS

| | | | |
|---|---|---|---|
| 5,094,942 | 3/1992 | Hashizuma et al. | 435/7.23 |
| 5,206,161 | 4/1993 | Drayna et al. | 435/212 |
| 5,364,934 | 11/1994 | Drayna et al. | 536/23.2 |
| 5,474,901 | 12/1995 | Drayna et al. | 435/7.4 |

FOREIGN PATENT DOCUMENTS 2268694  11/1990  Japan.

OTHER PUBLICATIONS

Rowland, M. and Tozer, TN. Clinical Pharmacokinetics: Concepts and Applications, Second Edition. Lea & Febiger, Philadelphia, pp. 9, 10, 54, 55, 132–134, 1989.

Khan, AR and James, MNG. Moleuclar mechanisms for the conversion of zymogens to active proteolytic enzymes. Protein Sci. &:815–836, 1998.

Bajzer L., et al., The fibrinolytic effect of activated protein C (APC) in plasma is specifically attributed to its ability to inhibit the activation of TAFI. Blood. 86:(10) Suppl. 1, Abstract No. 1420, Nov. 1995.

Bajzar, L., et al., Purification and characterization of TAFI, a thrombin–activatable inhibitor. J. Biol. Chem. 270(24):14477–14484, Jun. 1995.

Sheth et al., "Administration of a Humanized Monoclonal Antibody to Factor IX in Healthy Volunteers," *Blood* 92 (10) p. 362a (1998), Abstract #1491 only.

Blackburn et al., "Anti–factor IX Monoclonal Antibody, BC2, Is a Potent Antithrombotic Agent," *Blood* 90 (10) pp. 424a–425a (1997), Abstract #1885 only.

Blackburn et al., "Anti–factor IX Monoclonal Antibody: Extended Duration of Therapeutic Protection for Arterial Thrombosis," *Blood* 92 (10) p. 670a (1998), Abstract #2761 only.

Von dem Borne, P., et al., "Thrombin–Mediated Activation of factor XI Results in a TAFI or Carboxy–peptidase B Dependent Inhibition", *Blood 88,* (1996), 10 Suppl. 1 part 1–2, 469A.

Church, W., et al., "Functional effect of monoclonal antibodies . . . ", *J Cell Biochem Suppl 15 (Part E)*, (Mar. 16, 1991), p. 131.

Jenny, R., et al., "Immunochemical techniques for studying coagulation proteins" *Methods Enzymol.* (1993), 222:400–416.

Sangrar, W., et al., "Antifibrinolytic Effect of Recombinant . . . ", *Biochemistry,* (1995), 34:15:5151–5157.

Von dem Borne, P., et al., "Thrombin–Mediated Activation of factor XI Results in . . . " *J Clin Invest.* (May 15, 1997), 99:10:2323–2327.

Hoogendoorn, H., et al., "A qualitative and quantitative analysis of the activation . . . ", *Blood,* (Jun. 1, 1990), 75:11:2164–2171.

Taylor, F., et al., "Anticoagulant and fibrinolytic activities . . . ", *Blood,* (Apr. 1, 1992), 79:7:1720–1728.

Cote, H., et al., "Functional characterization of recombinant humna . . . " *J Biol. Chem.,* (Mar. 7, 1997) 272:10:6194–6200.

Bajzar, L., et al., "An antifibrinolytic mechanism describing the prothrombotic effect", *J. Biol. Chem.* (1996), 271:38:22949–22952.

Bajzar, L., et al., "TAFI, or plasma procarboxypeptidase B, couples . . . ", *J. Biol. Chem.,* (1996), 271:38: 16603–16608.

Fredenburgh, J., et al., "Lys–plasminogen is a significant intermediate . . . ", *J Biol Chem,* (Dec. 25, 1992) 267:36:26150–26156.

Boffa, M., et al., Characterization of recombinant TAFI expressed . . . *Abstract of the International Congress on Fibrinolysis and Thrombolysis,* Barcelona, Spain, Jun. 24–28 1996—Abstract.

Neisheim, M., et al., "Thrombin, Thrombomodulin and . . . ", Thrombosis and Haemostasis, (1997) 78:1:386–391.

Felez, J., et al., "Competition Between Plasminogen and Tissue . . . ", *Blood,* (1993), 82:8:2433–2441.

Mosesson, M., et al., "The assembly and structure of the fibrin clot", *Nouv Rev Fr Hematol,* (1992) 34:11–16.

Haber, F. et al., "Antibody–Targeted Throbolytic Agents", *Japanese Circulation Journal,* (1990) 54:345–353.

(List continued on next page.)

*Primary Examiner*—David Saunders
*Assistant Examiner*—Mary Beth Tung
*Attorney, Agent, or Firm*—Wolf, Greenfield & Sacks, P.C.

[57] ABSTRACT

Methods and products for the treatment of a disorder characterized by the cleavage of a C-terminal lysine or arginine from an intact peptide are provided. In the methods of the invention a peptide that inhibits the activation of thrombin-activatable fibrinolysis inhibitor (TAFI) is administered in an effective amount and in a pharmaceutically acceptable carrier to a subject having a disorder characterized by the cleavage of a C-terminal lysine or arginine from an intact peptide. The compositions are pharmaceutical compositions of peptides that inhibit the activation of TAFI. Also provided is a monoclonal antibody that binds TAFI zymogen but that does not bind to active TAFI and inhibits the activation of TAFI.

7 Claims, No Drawings

OTHER PUBLICATIONS

Takahashi, Hoyu, "Citculating Thrombomodulin as a Novel . . . " *American J Hematology,* (1992) 41:32–39.

Pixley, R., et al., "The Contact System Contributes to hypotension . . . ", *J. Clin. Invest.,* (1993) 91:61–68.

Horrevoets A., et al., "The Activation–resistant Conformation of Recombinant Human Plasminogen . . . " *J. Biological Chemistry,* (1995), 270:26:15770–15776.

Stevens, W., et al., "Calcium Ion Modulation of Meizothrombin . . . ", *J. Biological Chemistry,* (1996) 271:14:8062–8067.

Bajzar, L., et al., "The Provibrinolysis Effect of Activated Protein . . . ", Blood, (1996), 88:001–008.

Bajzar, L., et al., "The Activated Protein C–mediated Enhancement of Tissue–type", *J. Biological Chemistry,* (1990), 265:28:16948–16954.

Bajzar, L., et al., "The Effect of Activated Protein C on Fibrinolysis in . . . ", *J. Biological Chemistry,* (1993), 268:12:8608–8616.

Pryzdial, E., et al., "Prothrombinase Components Can Accelerate . . . ", *J. Biological Chemistry,* (1995), 270:30:17871–17877.

Bokisch, V., et al., "Anaphylatoxin Inactivator of Human Plasma: Its Isolation and . . . ", *J Clin, Invest.* (1970), 49:2427–2436.

Hesselvik, J., et al., "Protein C, Protein S and C4b–Binding . . . ", *Thrombosis and Haemostasis,* (1991) 65:2:126–129.

Keyt, B., et al., "The Carboxyl–terminal Domain (111–165) of Vascular Endothelial . . . ", *J. Biological Chemistry,* (1996), 271:13:7788–7795.

Durie, F., "Collagen–Induced Arthritis as a Model of Rheumatoid Arthritis", *Clinical Immunology and Immunopathology,* (1994), 73:1:11–18.

Fava, R., et al., "Vascular Permeability Factor/Endothelial Growth . . . ", *J. Exp. Med.,* (1994), 180:341–346.

Eaton, D., et al., "Isolation, Molecular Cloning, and Partial Characterization of a Novel . . . ", *J. Biological Chem.,* (1991), 266:32:21833–21838.

Redlitz, A., et al., "Inducible Carboxypeptidase Activity", *Circulation,* (1996), 93:7:1328–1330.

Delk, A., et al., "Radioimmunoassay of Active Pancreatic Enzymes in Sera . . . ", *Clin Chem.,* (1985), 31:8:1294–1300.

Valnickova, Z., et al., "Activated Human Plasma Carboxypeptidase . . . " *J. Biological Chem.,* (1996), 271:22:12937–12943.

Tan, A., et al., "Activation and Characterization of Procarboxypeptidase B . . . ", *Biochemistry,* (1995) 34:5811–5816.

Tang, L., et al., "Molecular Determinants of Acute Inflammatory . . . ", *J. Clin. Invest.,* (1996), 97:5:1329–1334.

Esmon, C., et al., "Thrombomodulin as a model of molecular . . . ", *The Faseb Journal,* (1995) 9:946–955.

Conway, E., et al., "Biologically Active Thrombomodulin Is . . . Arthritis", *Blood,* (1993) 81:3:726–733.

Takano, S., et al., "Plasma Thrombomodulin in Health and Diseases", *Blood,* (1990), 76:10:2024–2029.

METHODS AND COMPOSITIONS FOR INHIBITING THE ACTIVATION OF THROMBIN-ACTIVATABLE FIBRINOLYSIS INHIBITOR (TAFI)

This application claims priority to U.S. Provisional Application No. 60/030,721, entitled "Methods and Compositions for Inhibiting the Activation of Thrombin-Activatable Fibrinolysis Inhibitor (TAFI)", filed on Nov. 8, 1996.

GOVERNMENT SUPPORT

This work was supported at least in part by Grants HLP01-46703 from the National Institutes of Health and a Postdoctoral Research grant from Medical Research of Canada. Accordingly, the government may retain certain rights in this invention.

BACKGROUND OF THE INVENTION

Coagulation and fibrinolysis are physiological pathways which are involved in maintaining normal blood hemostasis in mammals. Under conditions in which a vascular injury occurs, the coagulation pathway is stimulated to form a blood clot to prevent the loss of blood. Immediately after the vascular injury occurs, blood platelets begin to aggregate at the site of injury forming a physical plug to stop the leakage. Additionally, the injured vessel undergoes vasoconstriction to reduce the blood flow to the area and fibrin begins to aggregate forming an insoluble network or clot which covers the ruptured area. Once the vessel has been repaired, the fibrinolysis pathway is stimulated to dissolve the clot.

The balance between the coagulation and the fibrinolytic pathways is essential to the protection of the mammal from excessive blood loss and excessive fibrin build-up in the vascular system which would prevent normal blood flow. When an imbalance is created between the coagulation and fibrinolytic pathways, the physiological result in the mammal is often the development of a serious disease state. When the imbalance in the pathways shifts towards excessive coagulation, the result is the development of thrombotic tendencies which are often manifested as heart attacks, strokes, deep vein thrombosis and myocardial infarcts. When the balance shifts towards excessive fibrinolysis and decreased coagulation, the result is hemorrhage.

The coagulation pathway comprises a series of enzymatic activations which result in the formation of a fibrin clot. The tetrameric complex known as prothrombinase is an essential enzyme in the coagulation pathway. Prothrombinase is composed of a negatively-charged surface, $Ca^{2+}$, factor Xa (the enzyme) and factor Va (essential cofactor). Loss or inactivation of factor Va or factor Xa results in a loss in prothrombinase activity. The active prothrombinase enzyme catalyzes the conversion of prothrombin to thrombin. Thrombin catalyzes the cleavage of fibrinogen releasing fibrinopeptides A and B resulting in the production of fibrin monomer which is capable of spontaneously polymerizing to form a clot.

The fibrinolytic pathway also comprises a series of enzymatic activations but which terminate in the solubilization of a fibrin clot resulting in the removal of fibrin clots after vascular injury repair. Plasminogen, which is the zymogen, or inactive, plasma form of plasmin, has an affinity for fibrin clots and forms complexes with fibrin throughout various regions of the porous fibrin network. Another protease, tissue plasminogen activator (t-PA) cleaves a specific bond within the plasminogen zymogen resulting in the formation of the active form of the enzyme, plasmin. t-PA, however, is a poor activator of plasminogen in the absence of fibrin. T-PA, in combination with the fibrin, is a potent activator of plasminogen. The resulting plasmin partially degrades fibrin exposing C-terminal lysines on the fibrin. This partially degraded fibrin is a particularly potent cofactor for the t-PA-induced activation of plasminogen. Further degradation leads to the solubilization and degradation of the fibrin clot.

Although thrombin is an essential component of the anticoagulation pathway (directly causing the cleavage of fibrinogen to fibrin), in the presence of a specific cofactor, thrombomodulin, thrombin assumes another role which leads to the downregulation of thrombin and thus the downregulation of the coagulation pathway. In the presence of thrombomodulin, which is a component of the blood vessel wall, thrombin develops a specificity for protein C and catalyzes the proteolytic activation of protein C to form serine protease activated protein C (APC). APC proteolytically inactivates the essential cofactors, factor Va and factor Villa resulting in the downregulation of the coagulation pathway. By inactivating cofactor Va, APC causes a loss in prothrombinase activity. Because active prothrombinase catalyzes the production of thrombin from prothrombin, the APC-induced loss in prothrombinase activity results in a decreased production of thrombin. The net result of this pathway is the negative feedback regulation of thrombin when thrombomodulin binds to thrombin.

Thrombin, thrombomodulin, and APC are critical factors in the balance between the coagulation and fibrinolytic pathways because in addition to being important components of the coagulation pathway, these components are also involved in the fibrinolytic pathway. Either high levels of thrombin and/or when thrombin is associated with the cofactor thrombomodulin, thrombin activates a fibrinolysis inhibitor, known as thrombin-activatable fibrinolysis inhibitor (TAFI, also known as procarboxypeptidase B, carboxypeptidase B, plasma carboxypeptidase B, carboxypeptidase U, or carboxypeptidase R). TAFI is ordinarily present in the plasma in a zymogen, or inactive, form. Thrombin/thrombomodulin catalyze the activation of TAFI to produce an active TAFI which has been demonstrated to inhibit fibrinolysis. Active TAFI inhibits plasminogen activation by removing C-terminal lysines from partially degraded fibrin. The fibrin which has been cleaved by active TAFI is less effective as a cofactor for a plasminogen activator, such as t-PA dependent activation of plasminogen, than non-cleaved fibrin. Because the potency of fibrin which is available to act as a cofactor is reduced, the amount of plasminogen activated to form plasmin is also reduced, thereby attenuating the solubilization of fibrin and the dissolution of fibrin clots. APC, which is also produced by thrombin/thrombomodulin, inhibits the activation of TAFI by inhibiting the production of thrombin (i.e., by the negative feedback loop-involving loss of prothrombinase activity). Therefore, thrombin, in the absence of thrombomodulin, is involved in the coagulation pathway and in the presence of thrombomodulin, thrombin is involved in the downregulation of the coagulation pathway and in promoting a balance between opposing factors which are involved in the regulation of fibrinolysis (active TAFI inhibits fibrinolysis and APC promotes fibrinolysis by inhibiting the activation of TAFI).

Current therapies for treating disorders associated with imbalances in the coagulation and fibrinolytic pathways involve many risks and must be carefully controlled so that the balance between the pathways is not shifted too far in the other direction. For example, thrombolytic agents such as plasminogen, streptokinase, staphylokinase, t-PA and urokinase are all agents which promote fibrinolysis when there is a risk of thrombosis, but each therapy is also associated with hemorrhagic toxicity. Hemorrhage due to thrombolytic agents results from two factors: (1) the lysis of fibrin at sites of vascular injury prior to the repair of the injury site which may cause bleeding; and (2) a systemic lytic state that results from the systemic formation of plasmin and destruction of other coagulation factors. Therefore, the administration of thrombolytic agents must be carefully monitored in order to provide enough therapeutic agent to result in the destruction of unwanted blood clots, but to prevent the administration of too much therapeutic agent which would cause hemorrhage. In cases of excessive bleeding when coagulants are administered to therapeutically aid in the repair of damaged tissue, there is a risk of forming blood clots due to an overactivation of the coagulation pathway.

SUMMARY OF THE INVENTION

Methods and compositions for treating a subject having a disorder characterized by the cleavage of a C-terminal lysine or arginine from an intact active TAFI substrate peptide are disclosed herein. According to the invention it was discovered that peptides which bind to TAFI zymogen and inhibit the activation of TAFI are useful for therapeutic purposes. Thrombin catalyzed by thrombomodulin converts TAFI zymogen to active TAFI by proteolytic cleavage. When this activation step occurs several physiological changes occur such as the inhibition of fibrinolysis. The active TAFI causes these changes by proteolytically cleaving peptide substrates having a C-terminal lysine or arginine. For example, active TAFI inhibits fibrinolysis by cleaving fibrin. The present invention involves the finding that peptides which bind to TAFI zymogen and inhibit the activation cleavage of TAFI zymogen (referred to hereinafter as the "activation of TAFI") are useful for therapeutic purposes such as the promotion of fibrinolysis.

In one aspect of the invention a method for treating a subject having a disorder characterized by the cleavage of a C-terminal lysine or arginine from an intact peptide is provided. A pharmaceutical composition containing a pharmaccutically acceptable carrier and an effective amount for treating the disorder of a peptide that binds to TAFI zymogen and inhibits activation of TAFI zymogen is administered to the subject. In one embodiment the method also includes the step of coadministering the pharmaceutical composition with a therapeutic agent, other than a peptide according to the invention, useful for the treatment of the disease characterized by cleavage of a C-terminal lysine or arginine. Preferably the disorder characterized by the cleavage of a C-terminal lysine or arginine from an intact peptide is thrombosis and the effective amount of the peptide is an effective amount for promoting fibrinolysis in vivo.

In another embodiment the disorder characterized by the cleavage of a C-terminal lysine or arginine from an intact peptide is selected from the group of disorders consisting of but not limited to arthritis, sepsis, thrombosis, stroke, deep vein thrombosis, and myocardial infarction.

In an embodiment of the invention the peptide is selected from the group consisting of an antibody and a functionally active antibody fragment. Preferably the peptide is a human or humanized antibody. More preferably the peptide is a monoclonal antibody.

According to another aspect of the invention pharmaceutical compositions for treating a disorder characterized by the cleavage of a C-terminal lysine or arginine from an intact peptide are provided. In one aspect of the invention the pharmaceutical composition includes an effective amount for treating the disorder of a peptide that inhibits activation of thrombin-activatable fibrinolysis inhibitor zymogen, and a physiologically acceptable carrier. In another aspect of the invention the pharmaceutical composition includes an effective amount for treating the disorder of a peptide which selectively binds to an activation region of a thrombin-activatable fibrinolysis inhibitor zymogen, wherein the peptide does not bind to active thrombin-activatable fibrinolysis inhibitor, and a pharmaceutically acceptable carrier.

In one embodiment the peptide of the compositions is selected from the group consisting of an antibody and a functionally active antibody fragment. Preferably the peptide is as described above. More preferably the peptide is a monoclonal antibody and the monoclonal antibody has an inhibitory concentration in a thrombin-activatable fibrinolysis inhibitor activation assay that results in at least 75% inhibition of thrombin-activatable fibrinolysis inhibitor activity in the assay and wherein the inhibitory concentration of the monoclonal antibody is between 75 nanomolar and 7.5 micromolar, inclusive. In another preferred embodiment the peptide is a functionally active antibody fragment and the functionally active antibody fragment has an inhibitory concentration in a thrombin-activatable fibrinolysis inhibitor activation assay that results in at least 75% inhibition of thrombin-activatable fibrinolysis inhibitor activity in the assay and wherein the inhibitory concentration of the functionally active antibody fragment is between 75 nanomolar and 7.5 micromolar, inclusive. In a preferred embodiment the antibody fragment comprises a fragment selected from the group consisting of an F(ab')$_2$ fragment and an Fab fragment.

According to another embodiment of the invention the effective amount of the peptide is an effective amount for promoting fibrinolysis in vivo.

According to yet another aspect of the invention a monoclonal antibody or functionally active fragment thereof is provided. The monoclonal antibody or functionally active fragment thereof according to the invention selectively binds to a thrombin-activatable fibrinolysis inhibitor zymogen and inhibits the activation of TAFI, and does not bind to active thrombin-activatable fibrinolysis inhibitor. Preferably the monoclonal antibody or functionally active fragment thereof is a human or humanized antibody. In another preferred embodiment the monoclonal antibody or functionally active fragment thereof is an antibody fragment selected from the group consisting of an F(ab')$_2$ fragment and an Fab fragment.

DETAILED DESCRIPTION OF THE INVENTION

The invention involves the novel finding that peptides which bind to TAFI zymogen and inhibit the activation of TAFI, are useful for a variety of therapeutic purposes.

TAFI is an enzyme which has two forms, a zymogen form and an active form. A "TAFI zymogen" as used herein is the inactive precursor of enzymatically active TAFI which is found circulating in the plasma. "Active TAFI" as used herein is the active enzyme produced by cleavage of TAFI zymogen by an activator, such as a complex of thrombomodulin and thrombin. Active TAFI alters the activity of peptide substrates by specifically cleaving the peptide substrates at the C-terminal lysine or arginine.

A peptide substrate of active TAFI which is of particular physiological significance is fibrin. By removing the C-terminal from fibrin, active TAFI alters the ability of the fibrin to function as a cofactor in the enzymatic activation of plasminogen. Plasminogen is involved in the fibrinolytic pathway and when plasminogen activation is inhibited by TAFI the fibrinolytic pathway also is inhibited. Inappropriate inhibition of the fibrinolytic pathway increases the susceptibility of a patient to the development of strokes, deep vein thrombosis and myocardial infarcts.

According to the novel finding of the invention, a peptide which binds to TAFI zymogen and inhibits the activation of TAFI zymogen, is useful in the promotion of fibrinolysis. By preventing the activation of TAFI, the peptide prevents the inhibition of the fibrinolytic pathway and thus allows the dissolution and removal of fibrin clots to occur. As a result, the peptides of the invention are useful in conjunction with conventional thrombolytic therapy, such as t-PA in addition to prophylactic treatment to minimize the susceptibility of patients to stroke, deep vein thrombosis, and myocardial infarction.

In addition to the promotion of fibrinolysis, the peptides which inhibit TAFI activation according to the methods and compositions of the invention, are also useful for other therapeutic purposes. The peptides are useful for other therapeutic purposes because active TAFI inactivates a variety of peptide substrates having various physiological functions and the peptides of the invention will function to inhibit active TAFI from inactivating such peptide substrates. The peptide substrates which are useful according to the invention are those substrates which have a C-terminal lysine or arginine exposed and which are cleaved by active TAFI. Peptide substrates can easily be tested without undue experimentation in vitro for their ability to be cleaved by active TAFI. Active TAFI cleaves peptides having a C-terminal arginine or lysine, resulting in the release of a free arginine or lysine. An assay which measures the release of free arginine or lysine is useful for determining whether a peptide is a substrate of active TAFI. For example the following assay measuring the release of arginine or lysine is useful for determining whether a peptide substrate having an exposed C-terminal lysine or arginine is capable of being cleaved by active TAFI.

A peptide substrate is incubated with active TAFI under optimal enzymatic conditions. For example, 25 ml of active TAFI (30 mmol/l) is added to 975 ml of substrate (approximately 400 mmol/l) in HBS with 0.01% Tween 80 and incubated at 22° C. The reaction is stopped at various time points over a 3 hour interval to produce data at several time points. The samples are then deproteinated by perchloric acid (0.2M) and neutralized with KOH. Free arginine and lysine in the supernatant is detected by the methods disclosed in Gaede and Greishaber, *Anal. Biochem.*, v. 66, 393–399 (1975) and Nakatami, et. al., *Anal. Biochem.*, v. 49, 225–231 (1972). 100 ml of supernatant or a standard solution containing known concentrations of arginine or lysine are added to the wells of a microtiter plate containing 80 ml of solution which includes (final concentration) 10 mM NADH and 1 mM either pyruvate (in the case of arginine assay) or a-ketoglutaric acid (in the case of lysine assay) in 0.05M HEPES buffer, pH 7.0. The reactions are initiated by the addition of 20 ml of a buffered solution of octopine dehydrogenase (0.5 unit) for the arginine assay or saccharopine dehydrogenase (0.1 unit) for lysine assay. The diminution of emission at 450 nm is then monitored over the next two hours in a fluorescence plate reader attached to a Perkin-Elmer model 50B spectrofluorimeter. The excitation and emission wavelengths are 340 nm and 450 nm, and a 430 nm cutoff filter is employed in the emission beam. The concentrations of arginine and lysine are determined according to standard curves which are constructed by plotting $DEm_{450}$ of the standard samples (using fibrin as a control) versus the concentration of arginine or lysine.

For example, fibrinopeptides A and B (FPA and FPB) both terminate with an arginine residue and are substrates of active TAFI. Active TAFI cleaves the C-terminal arginine residue from both FPA and FPB causing a reduction in the substrate activity. FPA and FPB have been implicated in the induction of the release of plasminogen activators from endothelial cells. Modification of FPA and FPB causes an alteration in the level of plasminogen activators available in the local area of the clot and thus inhibits fibrinolysis.

Vascular endothelial growth factor (VEGF) is another potential substrate for active TAFI. VEGF has been demonstrated to be either plasmin cleaved or alternatively spliced to produce a VEGF variant with a C-terminal arginine-110 (B. A. Keyt, *J. Biol. Chem.*, 271, 7788–7795 (1996)). The $VEGF_{arg-110}$ variant is a potential substrate for active TAFI in vivo. Because VEGF has been linked with arthritis (R. A. Farva, *J. Exp. Med.*, 180, 341–346 (1994); F. Durie, *Clin. Immunology and Immunopathology*, 73, 11–18 (1994)) inhibitors of TAFI activation would inhibit the enzymatic cleavage of the VEGF variant and prevent inflammation associated with arthritis. A specific assay for determining whether cleavage of a substrate like VEGF by active TAFI causes arthritis is described in F. Durie, *Clin. Immunology and Immunopathology*, 73, 11–18 (1994).

APC indirectly inhibits the activation of TAFI by down-regulation the production of thrombin through inactivation of a cofactor of prothrombinase. Therefore, APC has a similar effect on TAFI activation as do the peptides of the invention. The peptides of the invention, however, do not have the side effects associated with the inhibition of thrombin production caused by APC. APC is known to be involved in many diseases such as familial thrombophilia (Charles Asmon, FASEB, 9, 946–955 (1995)). Several peptide substrates having a C-terminal arginine or lysine have been implicated in some of the APC involved diseases. For example, bradykinin and anaphylatoxins (C3a, C5a) are both known to be involved in sepsis, a disease in which APC has been implicated. Both bradykinin and C3a and C5a are known to be inactivated by carboxypeptidase N which has a similar substrate specificity to active TAFI (e.g., Erdos, *Biochem. Pharmacol.* 11, 585–592 (1962); V. A. Bokisch, *J. Clin. Invest.*, 49, 2427–2436 (1970); F. Taylor, *J. Clin. Invest.*, 91, 61–68 (1993); and J. F. Hesselvik, *Thrombosis and Haemostasis*, 65, 126–129 (1991)). Active TAFI is potentially implicated in the disorders in which APC is known to be involved and in which peptide substrates for which active TAFI exhibits specificity are implicated as playing a role. Therefore, the C-terminal lysine and arginine peptides involved in these disorders are putative therapeutic peptide substrates of active TAFI.

A role for thrombomodulin in the activation of TAFI was identified. It is postulated that disorders related to thrombomodulin may result from TAFI activation. Thrombomodulin has been implicated in various diseases such as inflammation associated with arthritis (E. M. Conway, *Blood*, 81, 726–733 (1993), disseminated intravascular coagulation, thrombosis, and Fulminant hepatitis (H. Takahashi, *Amer. J. Hematology*, 41, 32–39 (1992) and S. Takano, *Blood*, 76, 2024–2029 (1990). Therefore, the C-terminal lysine and arginine peptides involved in these disorders are putative therapeutic peptide substrates of active TAFI.

In one aspect the invention encompasses a method for treating a subject having a disorder characterized by the cleavage of a C-terminal lysine or arginine from an intact peptide. The method involves the administration of a peptide that inhibits TAFI activation to a subject. By preventing TAFI activation the peptide effectively inhibits the cleavage of a C-terminal arginine or lysine residue from a peptide and causes a physiological result such as the promotion of fibrinolysis.

A "disorder characterized by the cleavage of a C-terminal lysine or arginine from an intact peptide" as used herein is a disorder in which the cleavage of a C-terminal lysine or arginine of a peptide substrate causes an adverse physiological result that contributes to a disease etiology. The inhibition of that cleavage reaction prevents, inhibits, halts, ameliorates or otherwise reduces the adverse consequences of that disease etiology. A reduction in the adverse consequences of the disease, therefore does not have to be a cure for the disorder but may be any measurable therapeutic improvement. A therapeutic improvement will vary depending on the disorder being treated, as will be recognized by one of skill in the art. For example when the disease being treated is arthritis, then a reduction in inflammation is an example or a measurable therapeutic improvement.

Disorders characterized by the cleavage of a C-terminal lysine or arginine include but are not limited to arthritis, sepsis, thrombosis, stroke, deep vein thrombosis, and myocardial infarction. Treatment of such disorders embraces prophylactic treatment to prevent the disorder from occurring as well as therapeutic treatment of an existing condition.

In a preferred embodiment of the invention the disorder characterized by the cleavage of a C-terminal lysine or arginine from an intact peptide is a disorder associated with attenuated fibrinolysis such as, thrombosis, stroke, deep vein thrombosis, and myocardial infarction. As discussed above normal maintenance of hematological systems is due to a careful balance between the coagulation and fibrinolytic cascades and when this relationship is altered hematological problems may arise. Decreases in fibrinolysis and/or increases in coagulation often result in thrombosis or embolism. The peptides of the invention promote fibrinolysis by inhibiting the activation of TAFI, and thus preventing the inhibition of fibrinolysis.

The peptides of the invention are particularly useful in achieving a normal balance between the coagulation and fibrinolytic cascades because the peptides directly affect the amount of fibrinolysis without affecting the coagulation cascade. Compounds which are known to promote fibrinolysis, such as APC, also affect aspects of the coagulation cascade by altering the activation of components such as thrombin. Agents which are conventionally used as thrombolytic therapy have risks associated with hemorrhage because they can shift the balance between the 2 cascades too far in the direction of anti-coagulation and profibrinolysis. The peptides of the invention are advantageous in the treatment of fibrinolysis because they only interact with a single component of the coagulation/fibrinolysis cascades, TAFI zymogen, and do not interfere with the coagulation cascade.

The method for treating a subject having a disorder characterized by the cleavage of a C-terminal lysine or arginine from an intact peptide involves the step of administering to the subject a peptide that inhibits activation of TAFI zymogen (i.e., reducing the activity to a statistically significant extent). Although the examples below are directed to a preferred embodiment of the invention, namely, antibody compositions and associated methods of use for inhibiting TAFI activation, it should be understood that this description is illustrative only and is not intended to limit the scope of the instant invention. Any peptide which binds to TAFI zymogen and inhibits activation of the TAFI zymogen is encompassed by the methods of the invention. For example the peptide of the invention includes antibodies and functionally active fragments of antibodies. The peptides of the invention also include antigen binding peptides, complementarity determining region peptides, framework region peptide and other non-antibody peptides exhibiting TAFI zymogen specificity.

In a preferred embodiment the peptide that inhibits the activation of TAFI zymogen is an antibody or a functionally active antibody fragment. Antibodies are well known to those of ordinary skill in the science of immunology. As used herein, the term "antibody" means not only intact antibody molecules but also fragments of antibody molecules retaining TAFI zymogen binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316–325 (1983)).

In one set of embodiments, the antibody useful according to the methods of the present invention is an intact, human anti-TAFI zymogen monoclonal antibody in an isolated form or in a pharmaceutical preparation. The preparation and use of an anti-TAFI zymogen monoclonal antibody is described more fully in the attached Examples. The following is a description of a method for developing a monoclonal antibody that interacts with and inhibits the activation of TAFI zymogen. The description is exemplary and is provided for illustrative purposes only.

Murine monoclonal antibodies may be made by any of the methods known in the art utilizing TAFI zymogen as an immunogen. An example of a method for producing murine monoclonals useful according to the invention is the following: Balb/c mice are immunized intraperitoneally with approximately 75 $\mu$g of purified TAFI in an complete Freund's adjuvant. Booster injections of approximately 25 $\mu$g TAFI in incomplete Freund's are administered on days 16 and 37 after the initial injection. On day 66, the mice receive booster injections of approximately 25 $\mu$g TAFI in the absence of adjuvant. Three days later, the mice are killed and the isolated spleen cells fused to murine myeloma NS-1 cells using polyethylene glycol by a procedure such as that described by Oi (Oi VT: Immunoglobulin-producing hybrid cell lines in Hezenberg LA (ed): selected methods in cellular biology, San Francisco, Calif., Freeman, (1980)). Hybridoma cells are selected using hypoxanthine, aminopterin, and thymidine and grown in culture. Fourteen days after fusion, hybridoma cells producing anti-TAFI MoAbs are identified using a solid-phase radioimmunoassay by capturing anti-TAFI antibodies from conditioned media with immobilized goat antimouse IgG followed by quantitation of specifically bound $^{125}$I-labeled TAFI. Hybridomas testing positive for antibodies against TAFI zymogen are subcloned by limiting dilution and retested. Ascites for the hybridomas is then prepared in pristane-primed BALB/c mice by injecting approximately 1×10$^6$ cells/mouse. Concentrates enriched in the selected monoclonal antibodies are produced from ascites fluid by gel filtration on S-200 and concentrated with (NH$_4$)SO$_4$. The pellets are dissolved in an appropriate storage solution such as 50% glycerol/H$_2$O and are stored at 4° C.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51–63 (Marcel Dekker, Inc, New York, 1987), and Boerner el al., *J. Immunol.*, 147:86–95 (1991). In addition to the conventional methods for preparing human monoclonals antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362:255–258 (1993), Bruggermann et al., *Year in Immuno.*, 7:33 (1993) and U.S. Pat. No. 5,569,825 issued to Lonberg).

An example of one method for producing human monoclonals useful according to the invention is the following: Peripheral Blood Lymphocytes (PBL) are isolated from healthy human donors using density centrifugation, and further separated into B, T and accessory (A) cells, described methods such as (Danielsson, L., Moller, S. A. & Borrebaeck, C. A. K. *Immunology* 61, 51–55 (1987)). PBL are fractionated into T and non-T cells by rosetting with 2-amino ethyl (isothiouronium bromide)-treated sheep red corpuscles, and the latter cell population is incubated on Petri dishes coated with fibronectin or autologous plasma. Non-adherent cells (B-cells) are decanted, and adherent cells (accessory cells) are removed by 10 mM EDTA. The B cells are stimulated with 50 µg *Staphylococcus aureus* Cowan I/ml and irradiated (2000R) T cells with 10 µg PWM/ml overnight. The accessory cells are stimulated with 5 IU gamma interferon/ml and 10 µm indomethacin. The cell populations are cultured in supplemented RPMI 1640 which contains 10% human AB serum at a cell ratio of 2:1:0.4 (Ti:B:A) for a total of 6 days. The antigenic dose of TAFI zymogen is 1 µg/ml. The culture is supplemented with recombinant IL-2 (5 U/ml) and sPWM-T (25% by vol.), produced by described methods such as (Danielsson, L., Moller, S. A. & Borrebaeck C. A. K. *Immunology* 61, 51–55 (1987)). T cells (10 cells/ml) suspended in serum-free RPMI 1640 are incubated with 2.5 mM freshly prepared Leu-OMe for 40 min at room temperature. The cells are then washed 3 times in RPMI 1640 containing 2% human AB serum.

In vitro immunized PBL (1 µg TAFI zymogen/ml) and malign fusion partner are mixed at a ratio of 2:1 and fused using 30% (HF2) or 45% (NS-1/Sp2/0) polyethylene glycol (molecular weight 1540) with 7% dimethylsulphoxide (Borrebaeck, C. A. K. Stand. J. Immunol. 18, 9–12 (1983)). The human x human hybrids are resuspended in supplemented RPMI 1640 containing 10% fetal calf serum, 1 mM sodium pyruvate, 132 µg oxaloacetic acid/ml, 100 µM hypoxanthine, 0.4 µM aminopterin, 16 µM thymidine and 15% by vol. HF2-conditioned medium. Mouse myeloma cells are fused and cloned, except that feeder cells are omitted. Both human x human and human x mouse hybrids are plated out in 24 well plates (0.7–1.0×10<6>cells/well). The hybridomas are screened for production of specific antibodies, using an enzyme immunoassay. To sum up, 96 microtiter wells are each coated with 0.3 µg TAFI zymogen by allowing the TAFI zymogen solution to dry in the well. Gelatin (0.1%) is then used I order to block the wells for 30 min. At 37° C. The hybridoma supernatant (100 µl/well) is added to the washed wells and allowed to react for 30 min. At 37° C. Peroxidase-conjugated anti-human Ig antibodies diluted in phosphate buffered saline solution containing 10% fetal calf serum (100 µl/well) are finally incubated for 60 min., and enzyme substrate (ABTS) are added to develop the immunoassay.

The methods of screening putative peptides, such as those produced by the above described procedures, which are useful according to the invention are described in more detail below.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinant of antibody specificity (a single Fd fragment may be associated with up to ten different light chains without altering antibody specificity). Isolated Fd fragments retain the ability to specifically bind to antigen epitopes.

Within the antigen-binding region of an antibody are complementarity determining regions (CDRs) which directly interact with the epitope of the antigen, and framework regions (FRs), which maintain the tertiary structure of the paratope (see, A. G. Clark, 1986 supra; Roitt, 1991 supra). In both the heavy chain Fd fragment and the light chain of the IgG immunoglobulins, there are four framework regions (FR1–FR4) separated respectively by three complementarity determining regions (CDR1–CDR3). The CDRs, and in particular the CDR3 region, and more particularly the heavy chain CDR3, are primarily responsible for antibody specificity.

The sequences of the antigen-binding Fab' portion of the anti-TAFI zymogen monoclonal antibodies identified as being useful according to the invention in the assays provided below, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit TAFI activation are identified. These non-human animal antibodies can be humanized for use in the treatment of a human subject in the methods according to the invention. An example of a method for humanizing a murine antibody is provided in PCT International Publication No. WO 92/04381 which teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-TAFI zymogen monoclonal antibody; chimeric antibodies in which the Fc and/or FR and/or CDR1 and/or CDR2 and/or light chain CDR3 regions of an anti-TAFI zymogen antibody have been replaced by homologous human or non-human sequences; chimeric F(ab')$_2$ fragment antibodies in which the FR and/or CDR1 and/or CDR2 and/or light chain CDR3 regions of an anti-TAFI zymogen antibody have been replaced by homologous human or non-human sequences; and chimeric Fab fragment antibodies in which the FR and/or CDR1 and/or CDR2 and/or light chain CDR3 regions have been replaced by homologous human or non-human sequences. Thus, those skilled in the art may alter an anti-TAFI zymogen antibody by the construction of CDR grafted or chimeric antibodies or antibody fragments containing, all or part thereof, of the disclosed heavy and light chain V-region CDR AA sequences (Jones et al., *Nature* 321:522, 1986; Verhoeyen et al., *Science* 39:1534, 1988 and Tempest et al., *Bio/Technology* 9:266, 1991), without destroying the specificity of the antibodies for TAFI zymogen. Such CDR grafted or chimeric antibodies or antibody fragments can be effective in inhibiting TAFI activation in animals (e.g. cattle) and humans.

The human monoclonal antibodies of the present invention include intact humanized anti-TAFI zymogen monoclonal antibodies in an isolated form or in a pharmaceutical preparation. A "humanized monoclonal antibody" as used herein is a human monoclonal antibody or functionally active fragment thereof having at least human constant regions. The following examples of methods for preparing humanized monoclonal antibodies that interact with TAFI zymogen and prevent the activation of TAFI are exemplary and are provided for illustrative purposes only.

Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

In preferred embodiments, the humanized antibodies of the invention are human monoclonal antibodies including at least the TAFI zymogen binding CDR3 region of human anti-TAFI zymogen monoclonal antibodies. As noted above, such humanized antibodies may be produced in which some or all of the FR regions of a non human anti-TAFI zymogen monoclonal antibody have been replaced by homologous human FR regions. In addition, the Fc portions may be replaced so as to produce IgA or IgM as well as human IgG antibodies bearing some or all of the CDRs of the non human anti-TAFI zymogen monoclonal antibody. Of particular importance is the inclusion of the non human anti-TAFI zymogen monoclonal antibody CDR3 region and, to a lesser extent, the other CDRs and portions of the framework regions of the non human anti-TAFI zymogen monoclonal antibody. Such humanized antibodies will have particular clinical utility in that they will specifically recognize TAFI zymogen but will not evoke an immune response in humans against the antibody itself. In a most preferred embodiment, a murine CDR is grafted into the framework region of a human antibody to prepare the "humanized antibody." See, e.g., L. Riechmann et al., Nature 332, 323 (1988); M. S. Neuberger et al., Nature 314,268 (1985) and EPA 0 239 400 (published Sep. 30, 1987).

Antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the anti-TAFI zymogen antibody. Some of the CDRs may be replaced as well. Again, however, it is preferred that at least the heavy chain CDR3 region of the anti-TAFI zymogen antibody be included in such chimeric antibodies and, to a lesser extent, it is also preferred that some or all of the other CDRs of anti-TAFI zymogen antibody be included. Such chimeric antibodies bearing non-human immunoglobulin sequences admixed with the CDRs of a human anti-TAFI zymogen monoclonal antibody are not preferred for use in humans and are particularly not preferred for extended use because they may evoke an immune response against the non-human sequences. They may, of course, be used for brief periods or in immunosuppressed individuals but, again, fully human antibodies are preferred. Because, however, such antibodies may be used for brief periods or in immunosuppressed subjects, chimeric antibodies bearing non-human mammalian Fc and FR sequences but including at least the anti-TAFI zymogen heavy chain CDR3 are contemplated as alternative embodiments of the present invention.

For inoculation or prophylactic uses, the antibodies of the present invention are preferably intact antibody molecules including the Fc region. Such intact antibodies will have longer half-lives than smaller fragment antibodies (e.g. Fab) and are more suitable for intravenous, intraperitoneal, intramuscular, intracavity, subcutaneous, or transdermal administration.

Fab fragments, including chimeric Fab fragments, are preferred in methods in which the peptides of the invention are administered directly to a local tissue environment. For example, the Fab fragments are preferred when the peptide of the invention is administered directly to the site of a fibrin clot. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as E. coli, whereas whole immunoglobulin antibody molecules require mammalian cells for their production in useful amounts. Production of Fabs in E. coli makes it possible to produce these antibody fragments in large fermenters which are less expensive than cell culture-derived products.

Smaller antibody fragments and small binding peptides having binding specificity for the TAFI zymogen which can be used to inhibit TAFI activation also are embraced within the present invention. For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated VH single domain, also have been reported (see, for example, Ward et al., Nature 341:644–646 (1989)).

TAFI binding peptides which are not antibodies also may easily be synthesized or produced by recombinant means by those of skill in the art. Methods for preparing or identifying peptides which bind to a particular target are well known in the art. Molecular imprinting, for instance, may used for the de novo construction of macromolecular structures such as peptides which bind to a particular molecule. See for example Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, *Trends in Biochem. Sci.,* 19(9) January 1994; and Wulff, G., in Polymeric Reagents and Catalysts (Ford, W. T., Ed.) ACS Symposium Series No. 308, pp 186–230, *American Chemical Society* (1986). One method for preparing mimics of TAFI binding peptides involves the steps of: (I) polymerization of functional monomers around a known TAFI binding peptide or the binding region of an anti-TAFI zymogen antibody (the template) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other TAFI binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a non-biodegradable backbone. Other methods for designing such molecules include for example drug design based on structure activity relationships which require the synthesis and evaluation of a number of compounds and molecular modeling.

Using routine procedures known to those of ordinary skill in the art, one can determine whether a peptide which binds to TAFI zymogen is useful according to the invention by determining whether the peptide is one which inhibits the activation of TAFI zymogen in a TAFI activation assay.

Peptides which bind to the TAFI zymogen may also be identified by conventional screening methods such as phage display procedures (e.g., methods described in Hart, et al., *J. Biol. Chem.* 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to TAFI zymogen are obtained by selecting those phages which express on their surface a ligand that binds to the TAFI zymogen. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to the TAFI zymogen. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to TAFI zymogen any known binding assay may be employed. For example, the peptide may be immobilized on a surface and then contacted with a labeled TAFI zymogen. The amount of TAFI zymogen which interacts with the peptide or the amount which does not bind to the peptide may then be quantiated to determine whether the peptide binds to TAFI zymogen.

It is also possible to use the anti-idiotype technology to produce monoclonal antibodies which mimic an epitope. For example, an anti-idiotypic monoclonal antibody made to the first screening antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

TAFI activation assays also can be performed to screen and or determine the binding of a peptide to TAFI zymogen and the ability of the bound peptide to inhibit TAFI activation. In a 25-$\mu$L reaction volume, TAFI zymogen (0.8 $\mu$mol/L final concentration) is incubated with thrombomodulin (40 nmol/L final concentration), Ca$^{2+}$ (5.0 mmol/L final concentration), and thrombin (8.0 nmol/L final concentration) in the presence and absence of the putative peptide for 10 minutes at 22° C. Thrombin is then inhibited by the addition of the Phe-Pro-Arg chloromethyl ketone (FPA-CK 50 nmol/L final concentration). The effect of the peptide on the activation of TAFI zymogen to produce active TAFI is determined by measuring the time course of hippuric acid formation. Hydrolysis of the chromogenic substrate, hipurryl arginine, indicates that active TAFI is present in the mixture. A negative control may be used by adding FPA-CK at the initiation of the reaction. In the negative control TAFI is not activated because the thrombin is inhibited from functioning. A positive control may be used by allowing the reaction to proceed in the absence of a peptide or inhibitor of TAFI activation. In the positive control TAFI is activated because the reaction is allowed to proceed uninhibited. The time course of hippuric acid formation is measured by first correcting the volume in each of the reactions by the addition of a volume of buffer equal to that of the added putative peptide. A 25-$\mu$L aliquot is removed from each of the reactions (30 $\mu$mol/L final concentration ) and added to 975 $\mu$l of hipurryl arginine (410 $\mu$mol/L) in HBS with 0.01% Tween 80. The time course of hippuric acid formation at 22° C. is followed by monitoring absorbance at 254 nm and 0.5 minute intervals using a spectrophotometer such as Beckman DU-65 spectrophotometer (Fullteron, Calif.).

Activation assays also can be used to assess the relative inhibitory concentrations of a peptide in an activation assay and to identify those peptides which inhibit activation by at least, e.g., 75% .

In addition to the above-described binding assays the following may also be employed to screen peptides, such as antibodies useful according to the invention. Once an antibody useful according to the invention is identified it is possible to produce anti-idiotypic antibodies which can be used to screen other monoclonal antibodies to identify whether the antibody has the same binding specificity as an antibody of the invention. Such anti-idiotypic antibodies can be produced using well-known hybridoma techniques (Kohler and Milstein, *Nature*, 256:495, 1975). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody which was identified (screening antibody). The immunized animal will recognize and respond to the idiotypic determinants of the screening antibody and produce an antibody to these idiotypic determinants. By using the anti-idiotypic antibodies of the immunized animal, which are specific for the screening antibody, it is possible to identify other clones with the same idiotype as the screening antibody. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the specificity for an epitope of TAFI zymogen which inhibits the activation of TAFI.

Other assays will be apparent to those of skill in the art, having read the present specification, which are useful for determining whether a peptide which binds to TAFI zymogen also inhibits TAFI activation.

According to the methods of the invention, the peptide may be administered in a pharmaceutically acceptable composition. In general, pharmaceutically-acceptable carriers for monoclonal antibodies, antibody fragments, and peptides are well-known to those of ordinary skill in the art. As used herein, a pharmaceutically-acceptable carrier means a nontoxic material that does not interfere with the effectiveness of the biological activity of the active ingredients, i.e., the ability of the peptide to inhibit TAFI zymogen activation. Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. The peptides of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces locally administering the compositions of the invention, including as implants.

According to the methods of the invention the peptides can be administered by injection by gradual infusion over time or by any other medically acceptable mode. The administration may, for example, be intravenous, intraperitoneal, intramuscular, intracavity, subcutaneous or transdermal. Preparations for parenteral administration includes sterile aqueous or nonaqueous solutions, suspensions and emulsions. Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

The compositions of the invention are administered in therapeutically effective amounts. As used herein, an "effective amount" of the peptide of the invention is a dosage which is sufficient to inhibit TAFI zymogen activation to an extent which will inhibit the increase in, maintain or even reduce the circulating levels of active TAFI. A reduction in the circulating levels of active TAFI is sufficient to produce the desired effect in which the symptoms associated with the physiological activity of active TAFI, such as an inhibition in fibrinolysis, are ameliorated or decreased. Preferably an effective amount of the peptide is an effective amount for promoting fibrinolysis in VIVO. A therapeutically effective amount is not, however, a dosage so large as to cause adverse side effects, such as hemorrhage associated with excessive fibrinolysis. Generally, a therapeutically effective amount may vary with the subject's age, condition, and sex, as well as the extent of the disease in the subject and can be determined by one of skill in the art. The dosage may be adjusted by the individual physician or veterinarian in the event of any complication. A therapeutically effective amount typically will vary from about 0.01 mg/kg to about 500 mg/kg, were typically from about 0.1 mg/kg to about 200 mg/kg, and often from about 0.2 mg/kg to about 20 mg/kg, in one or more dose administrations daily, for one or several days (depending of course of the mode of administration and the factors discussed above). A preferred concentration of the peptide is a concentration which is equimolar to the concentration of TAFI in the plasma of a subject. The normal plasma concentration of TAFI is 75 nanomolar.

One of skill in the art can determine what an effective amount of a peptide is by screening the ability of the peptide to inhibit the activation of TAFI in an in vitro assay. The affectivity of the peptide can be defined in terms of the ability of the peptide to inhibit TAFI activation. An exemplary assay for measuring the ability of a putative peptide of the invention to inhibit TAFI activation is provided in the Examples and has been discussed above. The exemplary assay is predictive of the ability of a peptide to inhibit TAFI activation in vivo and, hence, can be used to select peptides for therapeutic applications. The activation assay measures the ability of a peptide to inhibit TAFI activation. The peptides of the invention preferably exhibit an inhibitory concentration (between 75 nanomolar and 7.5 micromolar, inclusive) in a TAFI activation assay to result in at least between about 65–75% inhibition of TAFI activation in the assay. With respect to the in vitro activation assay disclosed in the Examples, a peptide useful according to the invention preferably has an inhibitory concentration which is between about 75 nanomolar and 7.5 micromolar, inclusive, to result in at least about 65–75% inhibition. One skilled in the art can use the assay to select peptides exhibiting a range of inhibitory activities. Thus, using no more than routine skill in the art, alternative peptides which exhibit inhibitory concentrations in an appropriate range can be identified. In a preferred embodiment, the peptide has an inhibitory concentration which results in at least 80%; more preferably, at least 85% and most preferably, at least 90% inhibition (at the above-described inhibitory concentrations) in the activation assay.

According to another embodiment of the methods of the invention a therapeutic agent other than the peptides of the invention but useful for the treatment of the disease characterized by cleavage of a C-terminal lysine or arginine may be administered together with the peptides of the invention in the pharmaceutical compositions. For example, when the disease being treated is a disease associated with the formation of blood clots, then a useful therapeutic agent is a clot dissolving agent. Drugs which are clot dissolvers include thrombolytic agents which have been used in the treatment of acute venous thromboembolism and pulmonary emboli and are well known in the art (e.g. see Hennekens et al, *J Am Coll Cardiol*; v. 25 (7 supp), p. 18S–22S (1995); Holmes, et al, *J Am Coll Cardiol*; v.25 (7 suppl), p. 10S–17S (1995)). Thrombolytic agents include, for example, direct acting agents such as streptokinase, staphylokinase, and urokinase, and second generation agents such as tissue plasminogen activator (tPA).

"T-PA" as used herein includes native t-PA and recombinant t-PA, as well as modified forms of t-PA that retain the enzymatic or fibrinolytic activities of native t-PA. The enzymatic activity of t-PA can be measured by assessing the ability of the molecule to convert plasminogen to plasmin. The fibrinolytic activity of t-PA may be determined by any in vitro clot lysis activity known in the art, such as the purified clot lysis assay described by Carlson, et. al., *Anal. Biochem.* 168, 428–435 (1988) and its modified form described by Bennett, W. F. Et al., 1991, Supra, the entire contents of which are hereby incorporated by reference.

Recombinant t-PA has been described extensively in the prior art. Several forms of recombinant t-PA are commercially available such as ACTIVASE®.

Modified forms of t-PA ("modified t-PA") have been characterized and are known to those skilled in the art. Modified t-PA includes, but is not limited to, variants having deleted or substituted amino acids or domains, variants conjugated to other molecules, and variants having modified glycosylation. Several preferred modified t-PAs have been described in PCT Publication No. W093/24635; EP 352,119; EP382174; and Suzuki et al., *J. Cardiovasc. Pharmacal.* 22, 834–840 (1993). Each of these references is hereby incorporated by reference.

Briefly, PCT Publication No. W093/24635 discloses t-PA variants having an extra glycosylation site at any of the amino acid positions 103–105 and the native glycosylation site removed at position 117 of the native human t-PA. The amino acid number refers to the amino acid in that position of the mature, wild-type t-PA polypeptide as disclosed in U.S. Pat. No. 4,766,075. These variants have extended circulatory half lives and exhibit substantially the same or improved fibrin binding affinity and fibrinolytic potency as compared to wild-type human t-PA. The disclosed variants may also include at least one amino acid substituted in the 296–299 position with alanine and/or a substitution of the amino acids at positions 274–277 of wild type t-PA (phenylalanine, arginine, isoleucine, lysine) with leucine, histidine, serine, and threonine, respectively. One particularly effective type of variant disclosed in the reference is a triple mutant variant of wild type t-PA. The first mutation in a triple mutant is the addition of one glycosylation site at least one of the amino acid positions 103–105 by e.g., substituting the native amino acid sequence 103 with an asparagine as part of an Asn-X-Ser or Asn-X-Thr tripeptidyl sequence, wherein X is any amino acid except proline. The second mutation involves the removal of a glycosylation site at native amino acid site 117 (Asn) and replacing it with another amino acid, preferably glutamine. The third mutation is the replacement of native amino acids 296–302 with other amino acids. The most effective of the triple mutant variants is the specific molecule, T103N, N117Q, KHRR (296–299) AAAA t-PA (TNK t-PA).

EP 352,119 discloses Vampire Bat t-PA's (Bat-Pa (H), (I), and (L)). Vampire bat-Pa's are variants of native t-PA having a variety of sequence modifications. Although the Bat-Pa variants are structurally distinct from t-PA because they lack the Kringle 2 domain and plasmin-sensitive processing site, these variants are functionally similar to native t-PA. They are however, more potent than native t-PA.

Suzuki et al., *J. Cardiovasc. Pharmacal.* 22, 834–840 (1993) disclose t-PA variants in which a cysteine at position 84 of the growth factor domain of native t-PA is replaced by serine (C84S t-PA). Although this variant retains the functional activity of native t-PA, it has been shown to have a longer in vivo half life than native t-PA.

Native t-PA is cleared from the plasma quite rapidly. At least one receptor in the liver is involved in the clearance of t-PA. [Bugelski, P. J. et al., *Throm. Res.* 53, 287–303 (1989); and Morton P. A. et al., *J. Biol. Chem.* 264, 7228–7235 (1989)]. The responsibility for clearance of the t-PA by the liver has been localized to the finger and growth factor domains as well as to the carbohydrate chains linked to the amino acid-backbone. [Collen et al., *Blood* 71, 216–219 (1988); Larsen et al., *Blood* 73, 1842–1850 (1989); and Lau et al., *Biotechnology* 6, 734 (1988)].

The rapid clearance of t-PA from the blood presents a problem to the therapeutic use of the drug because it becomes difficult to maintain adequate therapeutic levels of t-PA in the blood. As a result, patients in need of t-PA treatment must be given a continuous intravenous administration in order to maintain therapeutic levels of t-PA.

Researchers have attempted to develop functional t-PA molecules which have decreased clearance rates. The term "clearance rate" as used herein means the rate at which the t-PA is removed from the bloodstream. The clearance rate is measured with respect to native t-PA, such that decreased clearance rates indicate that the t-PA variant is cleared more slowly than native tPA, and increased clearance rates indicate that the t-PA variant is cleared more rapidly than native t-PA. As a result, several variants of t-PA have been developed which retain t-PA functionality but have reduced clearance rates.

T-PA variants having deleted or substituted amino acids or domains, have been found to have reduced clearance rates. These variants include t-PA molecules with deleted amino acids or domains, such as those described in Johannessen et al., *Throm. Haemonstas* 63, 54–59 (1990); Collen et al., 1988, Supra; and Sobel et al., *Circulation* 81, 1362–73 (1990); t-PA molecules which have amino acid substitutions in the regions of 63–72 and 42–49, such as those described in Ahem et al., *J. Biol. Chem.* 265, 5540 (1990); and t-PA molecules which have a glutamic acid substituted for the arginine at position 275 of the native t-PA molecule such as that described in Hotchkiss et al., *Throm. Haemost.*, 55, 491 (1987).

T-PA molecules conjugated to other molecules have also been found to have decreased clearance rates. For example, conjugation of t-PA to polyethylene-glycol has been shown to reduce the clearance rate of t-PA, as disclosed in EP-A304,3 11. Conjugation of a t-PA molecule to a monoclonal antibody has been shown to increase the half-life of t-PA in vivo. [EPA339,505].

Modification of glycosylation on native t-PA has also been found to have an affect on clearance rates of t-PA. WO89/11531 discloses several t-PA variants having additional glycosylation sites, which also have decreased clearance rates. In particular, the T103N extra-glycosylation t-PA mutant exhibited a decreased clearance rate which is five fold lower than native t-PA. Other research has described t-PA variants with reduced glycosylation, which also exhibit decreased clearance rates. (Martin et al., *Fibrinolysis* 4 (3), 9 (1990). Other references describing t-PA glycosylation variants having reduced clearance rates include Ahern et al., Supra, and Collen et al., 1988, Supra. Each of the above references is hereby incorporated by reference.

The invention also encompasses pharmaceutical compositions useful for treating a subject having a disorder characterized by the cleavage of a C-terminal lysine or arginine from an intact peptide. In one aspect of the invention a pharmaceutical composition of a peptide that inhibits the activation of TAFI zymogen and a physiologically acceptable carrier is provided. The peptide of the composition is the same as the peptide described above for the method claims. The peptide binds to a TAFI zymogen and inhibits the activation of TAFI.

The term "physiologically-acceptable" refers to a non-toxic material that is compatible with the biological systems such of a tissue or organism. The physiologically acceptable carrier must be sterile for in vivo administration. The characteristics of the carrier will depend on the route of administration. The characteristics of the carrier will depend on the route of administration.

In another aspect of the invention a pharmaceutical composition of a peptide which selectively binds to an activation region of a TAFI zymogen but that does not bind to active TAFI and that inhibits the activation of TAFI and a pharmaceutically acceptable carrier is provided. As used herein an "activation region of a TAFI zymogen" is any region of the TAFI zymogen molecule which is essential to the activation of the TAFI zymogen. When a peptide of the invention is bound to an activation region of TAFI zymogen the contact between the peptide and the activation region renders the TAFI zymogen incapable of activation.

In another aspect of the invention a pharmaceutical composition of a peptide which selectively binds to an activation region of a TAFI zymogen and that inhibits the activation of TAFI but that does not bind to active TAFI and a pharmaceutically acceptable carrier is provided. The "activation region" as used herein is a region of TAFI zymogen which is essential to the activation of TAFI such that when the TAFI zymogen is in contact with the peptides of the invention prevents the activation of TAFI.

In one embodiment of the invention the pharmaceutical compositions of the invention may also include a therapeutic agent useful for the treatment of a disease characterized by cleavage of a C-terminal lysine or arginine. The therapeutic agents useful in such a composition are described in detail above.

According to another aspect, the present invention provides a monoclonal antibody or active fragment thereof which selectively binds to a TAFI zymogen and inhibits the activation of TAFI zymogen but that does not bind to active TAFI. Preferably the monoclonal antibody or active fragment thereof is a fully human anti-TAFI zymogen monoclonal antibody. The monoclonal antibodies of the invention may be used in any of the methods of the invention.

The invention further provides detectably labeled, immobilized and toxin conjugated forms of the antibodies and fragments thereof. The antibodies may be labeled using radiolabels, fluorescent labels, enzyme labels, free radical labels, avidin-biotin labels, or bacteriophage labels, using techniques known to the art (Chard, *Laboratory Techniques in Biology*, "An Introduction to Radioimmunoassay and Related Techniques," North Holland Publishing Company (1978).

Typical fluorescent labels include fluorescein isothiocyanate, rhodamine, phycoerythrin, phycocyanin, allophycocyanin, and fluorescamine.

Typical chemiluminescent compounds include luminol, isoluminol, aromatic acridinium esters, imidazoles, and the oxalate esters.

Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase.

The materials for use in the TAFI activation assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention which selectively binds TAFI zymogen for use as a positive control in the assay. The kit may also have containers comprising TAFI zymogen (Eaton, D. L., *J. Biol. Chem.*, v. 266, 21833–21838 (1991)) and a substrate for detecting activation of TAFI. Additionally the kit may include containers for buffer(s) useful in the assay.

The compositions of the invention may be useful for a variety of purposes other than the therapeutic method discussed above. In one instance the peptides which are monoclonal antibodies that bind to TAFI zymogen but do not bind to active TAFI of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The peptides that bind to TAFI zymogen but do not bind to active TAFI of the invention can be bound to many different carriers and used to detect the presence of TAFI zymogen or to isolate and/or purify TAFI zymogen. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding peptides, or will be able to ascertain such, using routine experimentation.

For purposes of the invention, TAFI zymogen may be detected by the peptides of the invention when present in biological fluids and tissues. Any sample containing a detectable amount of TAFI zymogen can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis. Additionally the levels of TAFI zymogen can be compared to the levels of active TAFI in the biological fluid and tissues in the above described assays.

The peptides of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the peptides of the invention, or will be able to ascertain such, using routine experimentation. Furthermore, the binding of these labels to the peptides of the invention can be done using standard techniques common to those of ordinary skill in the art.

Another labeling technique which may result in greater sensitivity consists of coupling the peptides to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

The compositions of the invention may also be used in a method for inhibiting the activation of TAFI or in a method of inhibiting the cleavage a C-terminal lysine or arginine from an intact peptide in a cell. A TAFI zymogen is contacted with an effective amount of the peptide of the invention to inhibit the activation of TAFI or to inhibit the cleavage of a C-terminal lysine or arginine of the intact peptide.

EXAMPLES

Materials. Recombinant t-PA, Activase, was provided by Dr. G. Vehar of Genentech (South San Francisco, Calif.). The lyophilized powder was dissolved in water to give a final concentration of 1.0 mg/mL, from which working stock solutions were prepared as described previously. Plasma (Lot. No. Fact 915P1) was purchased from George King Biomedical (Overland Park, Kans.). A soluble form of thrombomodulin, Solulin, was provided by Dr. J. Morser of Berlex (Richmond, Calif.). The sheep polyclonal anti-TAFI antibody was provided by Hugh Hoogenroorn of Affinity Biologicals (Hamilton, Ontario, Canada), 2-Guanidinoethylmercaptosuccinic acid (GEMSA), a specific inhibitor of carboxypeptidase A- and B-like exopeptidases, was purchased from Sigma (St. Louis, Mo.).

Horseradish peroxidase (HRP) was purchased from Boehringer Mannheim (Laval, Quebec, Canada). PCPS vesicles (PC:PS 3:1) were prepared according to the method of Barenholz et al. Prothrombin was purified as described previously and used to prepare thrombin by a modification of the procedure of Lundblad et al., as described previously. Protein C was purified and then activated by incubation with thrombin in the presence of EDTA, as described previously. TAFI was purified as previously described. TAFI was radiolabeled with $^{125}$I using IODO-BEADS (Pierce, Rockford, Ill.) as directed by Pierce. Free and bound $^{125}$I were separated on SEPHADEX G-10 equilibrated in 10 mmol/L Tris, 0.15 mol/L NaCl, pH 7.4 (TBS) containing 1% bovine serum albumin (BSA-TBS). The column was developed with TBS. Fractions containing $^{125}$I-labeled TAFI were diluted 1:1 with glycerol and stored at −20° C.

Example 1
APC Shortens Lysis Time of Clots
Methods

Preparation of plasma for lysis assays. Pooled (3 to 4 donors) fresh frozen human plasma was purchased from Haematologic Technologies Inc. (Burlington, Vt.) and dialyzed against 4 L of 20 mmol/L HEPES, 150 mmol/L NaCl, pH 7.4 (HBS) at 4° C. with 4 changes overnight. The dialysate, termed normal human plasma (NHP), was stored at −70° C. in 2.0-mL aliquots. TAFI-deficient plasma (TdP) was produced by passing an aliquot, maximally 50 mL, of NHP over a 2.0-mL anti-TAFI affinity column (MoAbTAFI#16-Sepharose 4B) equilibrated in HBS. Depletion of TAFI was verified by Western blot analysis of a sample from each individual fraction. Only the flow-through fractions depleted of TAFI with an $A_{280}$ equal to the NHP loaded onto the column were pooled and subsequently stored in 2.0 mL aliquots at −70° C. Pooled plasma samples were also subjected to Western blotting and TAFI concentrations were quantified by ELISA. The data indicated that the affinity column comprising MoAbTAFI#16 is able to deplete TAFI from plasma. Furthermore, quantitation of TAFI by ELISA indicates that a single pass of plasma over the affinity column resulted in the removal of 99.9% of TAFI from plasma.

Lysis assay. The assay was performed by initially diluting the plasma, either NHP or TdP, with HBS such that the $A_{280}$ was 16, typically 1 part plasma to 2 parts buffer, and PCPS vesicles were added to a concentration of 10 $\mu$mol/L. Clots (10 $\mu$L) were formed by the addition of 91 $\mu$L of diluted plasma to wells of a microtiter plate containing separated 2-$\mu$L aliquots of thrombin/$Ca^{2+}$, (final concentrations of 6.0 nmol/L and 5 mmol/L, respectively) and tPA (final concentration, 294 pmol/L). The remaining 5.0 $\mu$L volume was composed of buffer for control experiments or buffer with APC, MoAbTAFI#16, GEMSA, or PTI at various concentrations, depending on the requirements of the experiment. When purified TAFI was added back to TdP, it was added directly to the diluted plasma. After adding the plasma to the microtiter wells, the plate was transferred to a THERMOMAX microtiter plate reader (Molecular Devices). Temperature was maintained at 37° C. and the turbidity was monitored at 405 nm and 2.5-minute intervals. Lysis profiles were generated by plotting $A_{405}$ as a function of time. Clotting occurring within the first 5 minutes is represented as an increase in turbidity, whereas fibrin dissolution correlates with a reduction in turbidity. Lysis time is defined as the time required to achieve the transition midpoint in the reduction from the maximum turbidity to baseline values.
Results APC shortens lysis time of clots formed from normal human plasma. A turbidometric lysis assay was used to determine the effect of APC on tPA-induced lysis of clots formed from normal human plasma. NHP dialyzed and diluted one-third with HBS was allowed to clot in the presence of thrombin, $Ca^{2+}$, PCPS vesicles, tPA, and various concentrations of APC (0 to 50 nmol/L). Clots were maintained at 37° C. and turbidity (absorbance at 405 nm) was monitored. Lysis profiles are represented as plots of turbidity as a function of time. Lysis time, defined as the time required to attain the transition midpoint of the lysis profiles, was determined for each lysis profile. The inverse dependence of lysis time on APC concentration confirms the profibrinolytic effect of APC (not shown). Lysis time decreased from 132.5 minutes in the absence of APC to 45 minutes in the presence of saturating concentrations of APC. However, APC could not overcome the prolongation of lysis by active TAFI. In this experiment, APC exhibits an $EC_{50}=4$ nmol/L and achieves saturation at less than 12.5 nmol/L. Furthermore, APC appears to inhibit the activation of TAFI and not that of active TAFI.

Example 2
Monoclonal Antibody to TAFI Zymogen Inhibits Activation of TAFI
Methods Production, characterization, and purification of the anti-TAFI MoAbs designated MoAbTAFI#13 and #16. Female, 6-week old Balb/c mice were immunized intraperitonically with 75 $\mu$g of purified TAFI in complete Freund's adjuvant. Booster injections of 25 $\mu$g TAFI in incomplete Freund's were administered on days 16 and 37 after the initial injection. On day 66, the mice received booster injections of 25 $\mu$g TAFI in the absence of adjuvant. Three days later, the mice were killed and the isolated spleen cells were fused to murine myeloma NS-1 cells using polyethylene glycol as described by Oi supra. Hybridoma cells were selected using hypoxanthine, aminopterin, and thymidine and grown in culture as described previously. Fourteen days after fusion, hybridoma cells producing anti-TAFI MoAbs were identified using a solid-phase radioimmunoassay by capturing anti-TAFI antibodies from conditioned media with immobilized goat antimouse IgG followed by quantitation of specifically bound $^{125}$I-labeled TAFI. Hybridomas testing positive for antibodies against TAFI were subcloned by limiting dilution and retested. Ascites for two hybridomas, designated MoAbTAFI#13 and MoAbTAFI#16, were prepared in pristane-primed BALB/c mice by injecting 1×10$^6$ cells/mouse. Concentrates enriched in MoAbTAFI#13 and #16 were produced from ascites fluid by gel filtration on S-200 and concentrated with $(NH_4)SO_4$. The pellets were dissolved in 50% glycerol/$H_2O$ and stored at 4° C.

Immobilization of MoAbTAFI#16 to Sepharose 4B. The concentrated MoAbTAFI#16 solution was diluted and dialyzed against 0.1 mol/L sodium citrate, pH 6.5, and then coupled to CNBr-activated SEPHAROSE 4B (Pharmacia, La Jolla, Calif.) by modification of the procedure of Cuarrecasas, as reported previously. Two milliliters of 2.5 mg/mL MoAbTAFI#16 was incubated with the activated Sepharose for 6 hours at 4° C. and for a further 8 hours after the addition of 0.4 mL 1.0 mol/L Tris, pH 8.0. This resulted in an 82% coupling efficiency producing a 2.0 mL column with 2.05 mg MoAbTAFI#16 per milliliter of Sepharose 4B resin.

Affinity purification and HRP conjugation of polyclonal anti-TAFI. The caprylic acid precipitated sheep antibodies were subjected to affinity purification by passing the antibodies dialyzed against 20 mmol/L HEPES, 150 mmol/L NaCl pH 7.4 over a 1.0 mL Sepharose CL-4B to which 1.0 mg of TAFI had been coupled. TAFI was coupled using the protocol described for immobilization of MoAbTAFI#16. Antibodies retained on the affinity column were eluted using Gentle Elution Buffer (Pierce). After extensive dialysis against HBS, affinity-purified antibodies were concentrated using an Amicon concentrator with a PY-10 filter (Amicon, Oakville, Ontario, Canada), diluted by the addition of an equal volume of glycerol, and stored at −20° C. HRP was conjugated to the polyclonal anti-TAFI IgG using a periodate coupling method. The HRP-coupled polyclonal anti-TAFI was precipitated by the addition of $(NH_4)_2SO_4/H_2O$ followed by centrifugation. The final pellet was dissolved in a volume of a 50% glycerol/$H_2O$ to yield a 1.0 mg/mL solution of HRP-conjugated polyclonal anti-TAFI, which was stored at −20° C.

Development of an enzyme-linked immutnosorbent assay (ELISA) for quantification of TAFI. Wells of a 96-well microtiter plate, Corning (Corning, N.Y.), were coated with MoAbTAFI#13 by incubating 10 $\mu$g/mL MoAbTAFI#13 in 50 mmol/L sodium carbonate, pH 9.6, for 2 hours at 22° C. Nonspecific sites were blocked with BSA. Samples were diluted in 0.1% BSA in HBS with 0.1% Tween 20 and 100 $\mu$L of each sample was applied to each well and incubated for 1.5 hours at 22° C. HRP-conjugated anti-TAFI was then incubated with each sample and specific binding was determined o-phenylene-daimine dihydrochloride (Sigma). The color was allowed to develop for 10 minutes. The reaction was then quenched by the addition of sulfuric acid to each well. Absorbance was measured at 490 nm and corrected by subtracting the absorbance at 650 nm using a THERMO-MAX microtiter plate reader (Molecular Devices, Sunnyvale, Calif.). Using this ELISA, the concentration of TAFI in a plasma pool ($\geq$60 donors) was determined to be 73 nmol/L, which compares favorably with a concentration of 50 nmol/L that was calculated based on recovery of activity during purification. Concentrations in plasma obtained from 6 volunteers ranged from 50 to 175 nmol/L.

Western blotting. Samples were diluted in sample preparation buffer (1% sodium dodecyl sulfate (SDS), 1% BME, and 10% glycerol electrophoresis (SDS-PAGE) using a 5% to 15% gradient gel in a mini-slab gel electrophoresis apparatus (Hoefer, Technical Marketing, Ottowa, Ontario, Canada) according to the procedure of Neville. Protein was then transferred to Nitrocellulose (Schleicher & Schuel, Keene, NH) at 500 mA for 1.0 hour using the electroblotting techniques described by Towbin et al. Nitrocellulose was blocked with 5% nonfat dry milk in 20 mmol/L Tris, 0.15 mol/L NaCl, 0.05% Tween 20 at pH 7.4 (TBS-T). TAFI antigen was probed for 1.0 hour with MoAbTAFI#13, which was dissolved in TBS-T to a concentration of 5$\mu$g/mL. MoAbTAFI#13 was probed for 1.0 hour with an HRP-conjugated horse antimouse IgG (Southern Biotechnologies) diluted 1 in 5,000 in TBS-T. The secondary antibody was detected by enhanced chemiluminescense (Chemiluminescence Detection Kit; DuPont) using X-O-MAT film (Kodak Scientific Imaging) and an M35A X-Omat processor (Eastman Kodak, Rochester, N.Y.).

Chromogenic assay for active TAFI. Hydrolysis of the chromogenic substrate, hipurryl arginine, was used to determine whether MoAbTAFI#16 inhibits active TAFI. In a 25-$\mu$L reaction volume, TAFI (0.8 $\mu$mol/L final concentration) was incubated with thrombomodulin (40 nmol/L final concentration), $Ca^{2+}$ (5.0 mmol/L final concentration), and thrombin (8.0 nmol/L final concentration) in the presence and absence of MoAbTAFI#16 (12.5 $\mu$mol/L) for 10 minutes at 22° C. Thrombin was then inhibited by the addition of the Phe-Pro-Arg chloromethyl ketone (EPA-CK 50 nmol/L final concentration). A negative control was produced by adding FPA-CK before initiation of the reaction by the addition of TAFI. The effect of MoAbTAFI#16 on the active TAFI was determined by the addition of the antibody subsequent to the activation of TAFI. The volume was corrected in each of the other 3 reactions by the addition of a volume of buffer equal to that of the added MoAbTAFI#16. A 25-$\mu$L aliquot was removed from each of the 4 reactions (30 $\mu$l final concentration) and added to 975 $\mu$l or hipurryl arginine (410 $\mu$mol/L) in HBS with 0.01% Tween 80. The time course of hippuric acid formation at 22° C. was followed by monitoring absorbance at 254 nm and 0.5 minute intervals using a Beckman DU-65 spectrophotometer (Fullteron, Calif.).

Results

MoAbTAFI#16 inhibits the activation of TAFI catalyzed by a complex comprising thrombin and thrombomodulin. The ability of MoAbTAFI#16, a MoAb raised against purified human TAFI, to inhibit activation of TAFI by thrombin in complex with thrombomodulin was assessed using a two-stage assay active TAFI activity generated for each set of conditions was monitored using the chromogenic substrate hippuryl arginine. No active TAFI activity was generated when either MoAbTAFI#16 or FPA-CK, a specific inhibitor of thrombin, was present during the incubation of TAFI with thrombin and thrombomodulin. However, the addition of MoAbTAFI#16 subsequent to activation was without effect on active TAFI activity, because the rate of hippuryl arginine hydrolysis was identical to the control rate. These date indicate that MoAbTAFI#16 does not inhibit active TAFI, but does prevent the activation of TAFI.

EXAMPLE 3

APC and Monoclonal Antibody to TAFI Zymogen Inhibit TAFI Activation Through a Common Pathway 1. The profibrinolytic effect of APC is abrogated by MoAbTAFI#16. The effect of MoAbTAFI#16 on tPA-induced lysis of clots formed from normal human plasma was investigated because it was able to inhibit the activation of TAFI in a purified system. Lysis times were determined from the turbidometric lysis profiles produced in the presence of various concentrations of MoAbTAFI#16 not shown. In the absence of the antibody, the lysis time was approximately 145 minutes. However, the lysis time decreased saturably with increasing concentrations of MoAbTAFI#16, exhibiting a minimum lysis time of 45 minutes in the presence of 80 nmol/L antibody. In the presence of 50 nmol/L APC, lysis time was also 45 minutes, however, the addition of 80 nmol/L MoAbTAFI#16 was unable to shorten lysis time any further.

2. TAFI is required to observe the profibrinolytic effect of A PC clots formed from plasma. Although we were able to show that 80 nmol/L MoAbTAFI#16 both mimicked the apparent profibrinolytic effect of APC and abrogated the profibrinolytic effect of APC in clots formed from NHP, we wished to determine the lysis time-dependence on the concentration of TAFI in both the presence and absence of APC. Therefore, the effect of APC on the lysis time of clots formed from TdP or TdP subsequently reconstituted with various concentrations of purified TAFI was determined. The lysis time in the presence and absence of 50 nmol/L APC was approximately 50 minutes, indicating both that APC has no effect on lysis time of clots produced from TdP and that the lysis time of TdP is comparable to the lysis time of clots formed from NHP in the presence of saturating concentrations of APC. In the absence of APC, lysis time of clots formed from TdP reconstituted with TAFI (0 to 60 nmol/L) exhibited a concentration-dependent prolongation from 50 to 180 minutes with an $EC_{50}$=10 nmol/L TAFI. However, a TAFI-dependent increase in clot lysis time was completely inhibited by 50 nmol/L APC, because the lysis time in the presence of APC remained invariant at 50 minutes over the range of TAFI concentrations studied. These data indicate that the profibrinolytic effect of APC is not apparent in TdP, however, it can be reconstituted in TdP by the addition of purified TAFI. Therefore, the profibrinolytic effect of APC in clots formed from plasma, as quantified using a turbidometric lysis assay, is due solely to a mechanism involving TAFI. The data also indicate that as little as 3 nmol/L TAFI is required to observe an APC-dependent profibrinolytic effect. Furthermore, the TAFI-dependent prolongation of lysis time approaches saturation with 60 nmol/L TAFI, which is within the physiologic range of concentrations determined immunologically and is similar to the concentration calculated based on recovery of activity during purification.

3. Comparison of APC to inhibitors of carboxypeptidase B-like proteases (GEMSA and PTI) and MoAbTAFI#16 in their ability to enhance lysis time of clots formed from human plasma. The antifibrinolytic effect of TAFI can be overcome in at least three ways: by preventing the formation of its activator, thrombin; by preventing the activation of TAFI; and by inhibiting active TAFI. Therefore, the efficacy of APC, an inhibitor of thrombin formation; MoAbTAFI#16, an inhibitor of TAFI activation; and GEMSA and PTI, inhibitors of carboxypeptidase B-like enzymes, to inhibit the TAFI-dependent antifibrinolytic effect on lysis time was investigated. The TAFI-dependent profibrinolytic effect of each compound was evaluated by determination of lysis time of clots formed from both NHP and TdP in the presence of various concentrations of each inhibitor. APC, GEMSA, and MoAbTAFI#16 at every concentration studied did not affect lysis time of clots formed from TdP. In general, the lysis time remained fairly constant at approximately 50 minutes, indicating that none of the inhibitors used exhibited TAFI-independent effects on lysis time. However, the data (not shown) indicate that, in clots formed from NHP, each inhibitor was able to decrease lysis time from 140 to 50 minutes in a concentration-dependent manner. The lysis time at saturating concentrations of each inhibitor exhibited a minimum lysis time (average, 50 minutes) that is identical to the lysis time of clots formed from TdP for every concentration of each inhibitor. Although the magnitude of the profibrinolytic effect was 90 minutes for each inhibitor, the $EC_{50}$ associated with each one varied greatly. APC was most potent ($EC_{50}$=5 nmol/L), followed by MoAbTAFI#16 ($EC_{50}$=15 nmol/L), PTI($EC_{50}$=50 nmol/L), and finally GEMSA ($EC_{50}$=90 $\mu$nmol/L). These data indicate that a shortening of lysis time can be achieved at various stages in the activation of TAFI.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety herein by reference.

We claim:

1. A method for treating a subject having a disorder wherein a C-terminal lysine or arginine is cleaved from an intact peptide comprising:

administering to a subject having a disorder wherein a C-terminal lysine or arginine is cleaved from an intact peptide a pharmaceutical composition containing a pharmaceutically acceptable carrier and an effective amount for treating the disorder of a peptide that binds to TAFI zymogen and inhibits activation of thrombin-activatable fibrinolysis inhibitor zymogen, wherein the peptide that binds to TAFI zymogen and inhibits activation of thrombin-activatable fibrinolysis inhibitor zymogen is selected from the group consisting of an antibody and a functionally active fragment.

2. The method of claim 1, further comprising coadministering a therapeutic agent useful for the treatment of the disorder wherein a C-terminal lysine or arginine is cleaved.

3. The method of claim 1, wherein the disorder in which a C-terminal lysine or arginine is cleaved from an intact peptide is selected from the group of disorders consisting of arthritis, sepsis, thrombosis, strokes, deep vein thrombosis, and myocardial infarctions.

4. The method of claim 1, wherein the peptide that binds to TAFI zymogen and inhibits activation of thrombin-activatable fibrinolysis inhibitor zymogen is a humanized antibody.

5. The method of claim 1, wherein the peptide that binds to TAFI zymogen and inhibits activation of thrombin-activatable fibrinolysis inhibitor zymogen is a monoclonal antibody.

6. The method of claim 3 wherein the disorder in which a C-terminal lysine or arginine is cleaved from an intact peptide is thrombosis.

7. The method of claim 6, wherein the effective amount of the peptide that binds to TAFI zymogen and inhibits activation of thrombin-activatable fibrinolysis inhibitor zymogen is an effective amount for promoting fibrinolysis in vivo.

* * * * *